US011779776B2

(12) United States Patent
Ramaswamy et al.

(10) Patent No.: US 11,779,776 B2
(45) Date of Patent: Oct. 10, 2023

(54) SYSTEMS AND METHODS FOR DECALCIFYING CARDIAC VALVES AND VESSELS

(71) Applicants: Sharan D. Ramaswamy, Miami, FL (US); Markondeyaraj Pulugurtha, Miami, FL (US)

(72) Inventors: Sharan D. Ramaswamy, Miami, FL (US); Markondeyaraj Pulugurtha, Miami, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 18/184,330

(22) Filed: Mar. 15, 2023

(65) Prior Publication Data
US 2023/0241406 A1 Aug. 3, 2023

Related U.S. Application Data

(62) Division of application No. 17/817,085, filed on Aug. 3, 2022, now Pat. No. 11,648,414.

(60) Provisional application No. 63/228,952, filed on Aug. 3, 2021.

(51) Int. Cl.
*A61N 2/02* (2006.01)
*A61N 2/00* (2006.01)
(52) U.S. Cl.
CPC ............... *A61N 2/02* (2013.01); *A61N 2/004* (2013.01)
(58) Field of Classification Search
CPC .................. A61N 2/02; A61N 2/004

USPC ......................................... 600/9–15
See application file for complete search history.

(56) References Cited

U.S. PATENT DOCUMENTS

| 6,030,334 A | 2/2000 | Cox et al. |
|---|---|---|
| 2005/0080459 A1 | 4/2005 | Jacobson et al. |
| 2005/0228417 A1 | 10/2005 | Teitelbaum et al. |
| 2006/0041182 A1 | 2/2006 | Forbes et al. |
| 2008/0103440 A1* | 5/2008 | Ferren ............... A61B 17/295 604/95.01 |
| 2009/0018486 A1* | 1/2009 | Goren ............... A61M 29/02 604/509 |
| 2009/0062828 A1 | 3/2009 | Marr |
| 2009/0065100 A1 | 3/2009 | Yoshizawa et al. |
| 2009/0209900 A1* | 8/2009 | Carmeli ........... A61B 17/22012 600/12 |

(Continued)

OTHER PUBLICATIONS

Iacopi, F., Van Hove, M., Charles, M. et al. Power electronics with wide bandgap materials: Toward greener, more efficient technologies. MRS Bulletin 40, 390-395 (2015). https://doi.org/10.1557/mrs.2015.71 (Year: 2015).

*Primary Examiner* — Sunita Reddy
(74) *Attorney, Agent, or Firm* — Saliwanchik, Lloyd & Eisenschenk

(57) ABSTRACT

Provided are systems and methods for decalcifying aortic valves and/or other valves, blood vessels, and/or cardiac tissues in a mammalian (e.g., a human) patient (e.g., a patient having or suspected of having calcific aortic valve disease (CAVD)). A transcatheter (aortic) valve decalcification system/method can include applying one or more pulsed magnetic fields to the calcium deposit(s) within a valve or other vessel or tissue within the patient. The system can include a catheter having pulsed magnetic field ribbons disposed therein, and the catheter can be provided to the patient.

17 Claims, 3 Drawing Sheets

(56) References Cited

U.S. PATENT DOCUMENTS

| | | |
|---|---|---|
| 2010/0268199 A1 | 10/2010 | Hyde et al. |
| 2011/0071335 A1 | 3/2011 | Ueda et al. |
| 2013/0317279 A1 | 11/2013 | Khizroev et al. |
| 2014/0081072 A1 | 3/2014 | Huang et al. |
| 2015/0080922 A1 | 3/2015 | Meinke et al. |
| 2021/0077821 A1 | 3/2021 | De Clerck |
| 2021/0161639 A1 | 6/2021 | Walzman |

* cited by examiner

Coils handle up to 7 A;

1 A yielded 100 Gauss increments at 2 cm in the initial experiment
- Typical field at 5.5 A is 500 Gauss
- With switching at 100-200 Hz, this gives a field of 5-10 Tesla/second System can handle 5.58 A with 20 °C raise in temperature
- Resulted in 3000 Gauss inside the core;
- Hardware under 43 °C (tissue is not in contact, so will not be affected)

SYSTEMS AND METHODS FOR DECALCIFYING CARDIAC VALVES AND VESSELS

CROSS-REFERENCE TO RELATED APPLICATIONS

The present is a divisional application of U.S. patent application Ser. No. 17/817,085, filed Aug. 3, 2022, which claims the benefit of U.S. Provisional Application Ser. No. 63/228,952, filed Aug. 3, 2021, the disclosures of each of which are hereby incorporated by reference in their entirety, including all figures, tables, or drawings.

BACKGROUND

Calcific aortic valve disease (CAVD) is projected to reach epidemic levels worldwide, and roughly a third of the global population aged 65 or older is expected to exhibit clinical signs of CAVD. Risk factors for CAVD include older age, genetics, use of tobacco products, rheumatic fever, and high blood pressure. Left untreated, CAVD leads to critical valve malfunction, typically via narrowing or stenosis of the aortic valve, which substantially augments the workload of the left ventricle; in due course, this leads to heart failure, with recent estimates reporting about 17,000 deaths/year in the United States. Artificial valve replacement via open-heart surgery or transcatheter aortic valve replacement (TAVR) are the only viable interventions currently available for critical CAVD. However, many patients are not suited for mechanical valves, which require anticoagulants. While bioprosthetic replacement valves made of animal tissues do not require blood thinners, they only last between 8 to 15 years. Valve replacement is also a relatively expensive process with an average total cost of roughly $170,000/procedure.

BRIEF SUMMARY

Embodiments of the subject invention provide novel and advantageous systems and methods for decalcifying aortic valves and/or other valves, blood vessels, and/or cardiac tissues in a mammalian (e.g., a human) patient (e.g., a patient having or suspected of having calcific aortic valve disease (CAVD)). A transcatheter aortic valve decalcification system/method can include applying one or more pulsed magnetic fields to the calcium deposit(s) within a valve or other vessel or tissue within a mammalian (e.g., a human) patient. The system can include a catheter having pulsed magnetic field ribbons disposed therein, and the catheter can be provided to the patient. The catheter can also include one or more filters to entrap particles spatially and/or one or more balloons to capture de-calcified particles of the valve, vessel, or tis sue.

In an embodiment, a system for decalcifying an internal structure of a patient can comprise: a catheter configured to be inserted into the internal structure of the patient; a plurality of pulsed magnetic field ribbons disposed in the catheter; and at least one filter disposed in the catheter and configured to entrap de-calcified particles spatially. As will be apparent to one of ordinary skill in the art, the pulsed magnetic field ribbons can be disposed in a wall of the catheter. The system can further comprise at least one balloon disposed in the catheter and configured to capture de-calcified particles. As will be apparent to one of ordinary skill in the art, the balloon can expand and block an interior of the catheter, such that de-calcified particles are removed when the balloon is removed. The pulsed magnetic field ribbons can be nanocrystalline magnetic ribbons (e.g., soft nanocrystalline magnetic ribbons that need low ampere-turns and/or low power to achieve a required magnetic field). The system can further comprise a magnetic field generator configured to provide (e.g., wirelessly) a magnetic field to the plurality of pulsed magnetic field ribbons while the catheter is inserted into the internal structure of the patient. The system can further comprise a programmable high-density power supply in operable communication with the magnetic field generator. The programmable high-density power supply can comprise at least one wide-bandgap semiconductor (e.g., at least one gallium nitride (GaN) semiconductor). The internal structure can comprise or be a valve (e.g., an aortic or other cardiac valve), a vessel (e.g., a blood vessel), and/or a cardiac tissue. The patient can be a mammalian patient (e.g., a human patient).

In another embodiment, a method for decalcifying an internal structure of a patient can comprise: inserting a catheter into the internal structure of the patient, the catheter comprising a plurality of pulsed magnetic field ribbons and at least one filter disposed therein, the at least one filter disposed being configured to entrap de-calcified particles spatially, and the internal structure having calcium compounds therein; providing a magnetic field to the plurality of pulsed magnetic field ribbons so the plurality of pulsed magnetic field ribbons release stored energy and destabilize the calcium compounds into forming the de-calcified particles; entrapping at least a portion of the de-calcified particles with the at least one filter; and removing the catheter from the internal structure of the patient. The system can further comprise at least one balloon disposed in the catheter and configured to capture de-calcified particles, and the method can further comprise, before removing the catheter from the internal structure of the patient, capturing at least a portion of the de-calcified particles with the at least one filter. The pulsed magnetic field ribbons can be nanocrystalline magnetic ribbons (e.g., soft nanocrystalline magnetic ribbons that need low ampere-turns and/or low power to achieve a required magnetic field). The system can further comprise a magnetic field generator that provides (e.g., wirelessly) the magnetic field to the plurality of pulsed magnetic field ribbons while the catheter is inserted into the internal structure of the patient. The system can further comprise a programmable high-density power supply in operable communication with the magnetic field generator. The programmable high-density power supply can comprise at least one wide-bandgap semiconductor (e.g., at least one gallium nitride (GaN) semiconductor). The internal structure can comprise or be a valve (e.g., an aortic or other cardiac valve), a vessel (e.g., a blood vessel), and/or a cardiac tissue. The patient can be a mammalian patient (e.g., a human patient).

BRIEF DESCRIPTION OF DRAWINGS

FIG. 2(a) shows a heart valve tissue that was left untreated while FIG. 2(b) shows a heart valve tissue that was treated (after the culturing) with a pulsed magnetic field. After treatment of the sample in FIG. 2(b), both samples (from FIG. 2(a) and from FIG. 2(b) were simultaneously processed histologically using Alizarin red staining, resulting in the images of FIGS. 2(a) and 2(b). In FIGS. 2(a) and 2(b), red stains indicate regions of high calcification. In the treatment for the tissue in FIG. 2(b), a pulsed magnetic field of 50 Gauss (frequency of 5 Hertz (Hz) and potential of 5 Volts (V)) and 300 Gauss (1 Hz, 22 V) were used for 30 minutes each.

DETAILED DESCRIPTION

Figure 1:
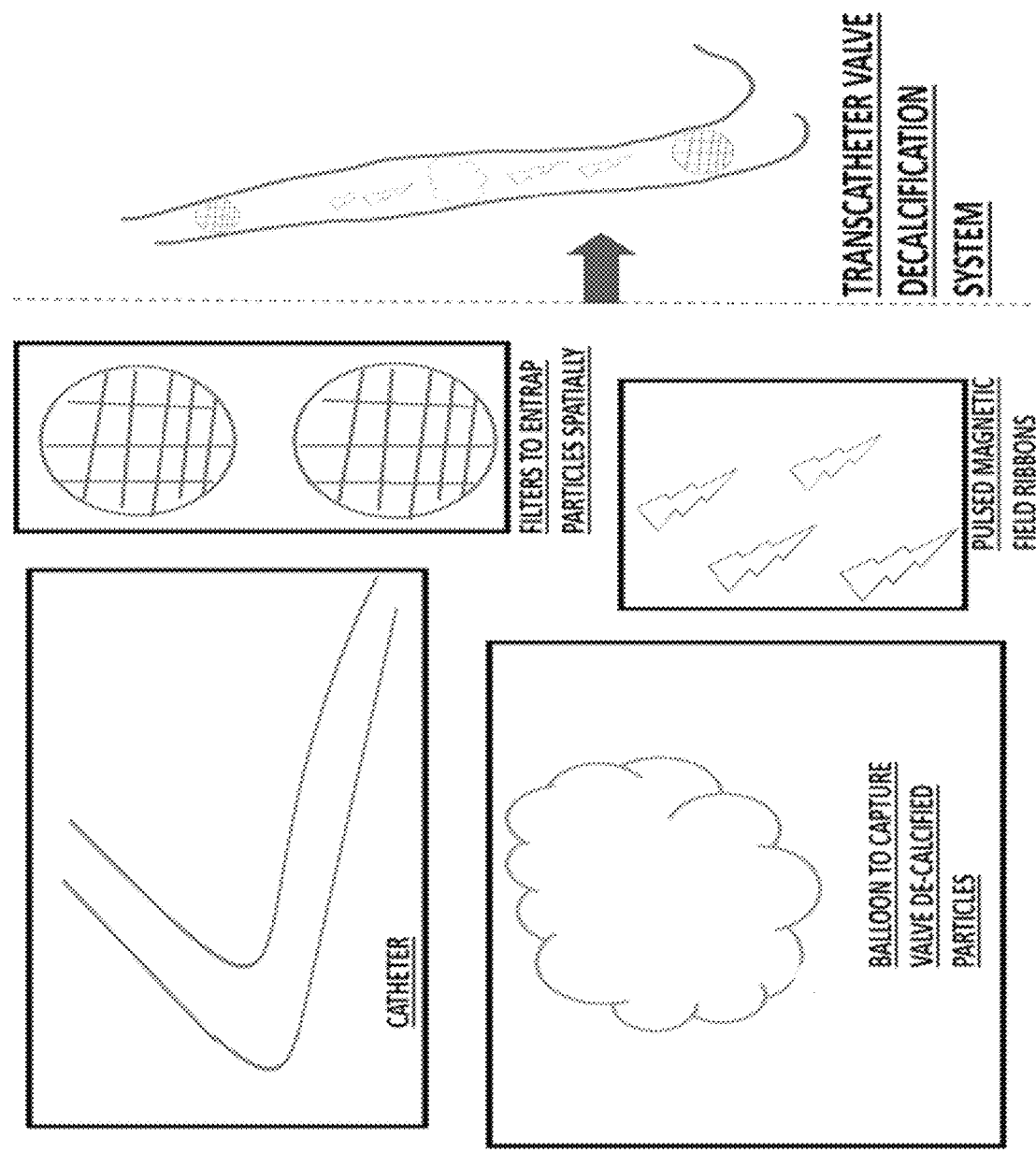
FIG. 1 is a schematic view of a transcatheter aortic valve decalcification system according to an embodiment of the subject invention.

Embodiments of the subject invention provide novel and advantageous systems and methods for decalcifying aortic valves and/or other valves, blood vessels, and/or cardiac tissues in a mammalian (e.g., a human) patient (e.g., a patient having or suspected of having calcific aortic valve disease (CAVD)). A transcatheter (aortic) valve decalcification system/method can include applying one or more pulsed magnetic fields to the calcium deposit(s) within a valve or other vessel or tissue within a mammalian (e.g., a human) patient. The system can include a catheter having pulsed magnetic field ribbons disposed therein, and the catheter can be provided to the patient. The catheter can also include one or more filters to entrap particles spatially and/or one or more balloons to capture de-calcified particles of the valve, vessel, or tissue.

In view of the concerns regarding CAVD discussed in the Background above, more effective management of CAVD is needed to avoid or delay the requirement for aortic heart valve replacement. This requires either novel pharmaceutical interventions that can reduce the rate of calcium deposition or technological developments that can safely remove the calcified deposits on the native aortic valve, thereby restoring its function of facilitating adequate unidirectional blood flow in the systemic circulation.

Owing to the global concern of rising rates in CAVD, much attention has been directed towards the mechanisms of calcification on aortic valve leaflets, but the initiators of CAVD still remain unclear. Though, valve calcification is an active and highly regulated process whose severity substantially increases with age, especially for those who are 75 and above. This suggests that in most cases, the build-up of calcific depositions that leads to critical valve malfunction and, therefore, the need for valve replacement, is an accumulative process that occurs over decades. If these calcified deposits can be safely removed from the affected valve, it is hence possible that the valve function will be restored, with subsequent calcific build-up leading to a recurring valve malfunction only after several years.

Pulsed magnetic fields (PMF) have several therapeutic benefits. Magnetic field therapies may also help address cardiovascular diseases through several potential mechanisms that involve remote cell differentiation, enhanced cell activity, and enhanced tissue remodeling. In nonmedical applications such as wastewater treatment, magnetic fields can help destabilize the calcium compounds and suppress their nucleation and growth while promoting the dissolution (see, e.g.; Lin et al., A critical review of the application of electromagnetic fields for scaling control in water systems: mechanisms, characterization, and operation, npj Clean Water 3, 1-19, 2020; and Alimi et al., Effect of a magnetic water treatment on homogeneous and heterogeneous precipitation of calcium carbonate, Desalination 206, 163-168, 2007; both of which are hereby incorporated by reference herein in their entireties). Embodiments of the subject invention are therefore based on the concept that an effective pulsed magnetic field transcatheter system can be used for aortic valve decalcification. This is supported based on the obtained data that shows that the magnetic field therapy does remove calcific deposits from heart valve tissues (see Examples 1-3).

FIG. 1 shows a schematic view of a transcatheter aortic valve decalcification system according to an embodiment of the subject invention. Referring to FIG. 1, a catheter can have pulsed magnetic ribbons disposed therein. The catheter can also have one or more filters to entrap particles spatially and/or one or more balloons to capture de-calcified particles (of the valve, vessel, or tissue). The catheter can be provided to the patient (e.g., a mammalian patient, such as a human patient, having or suspected of having CAVD).

The magnetic ribbons can be, for example, nanocrystalline magnetic ribbons (e.g., soft nanocrystalline magnetic ribbons that need low ampere-turns and/or low power to achieve the required field). The term "soft" (when referring to "soft" nanocrystalline magnetic ribbons) refers to the ability of magnetic domains to orient with weak magnetic fields to generate strong magnetization fields. The input field can be reported in ampere-turns or ampere/meter (A/m). Nanocrytalline or amorphous ribbons can generate 1.5 Tesla (T) to 2 T of field with 200 A/m or 2.5 Oersted (Oe). With coil resistance of 0.1 Ohms ($\Omega$)-10$\Omega$ and currents as low as 0.1 Amperes (A)-1 A and amp-turns of 0.1-1, a power of 0.1 Watts (W)-10 W can be targeted to generate magnetic fields of above 1 Tesla per second (T/s) at the tip of the catheter.

The magnetic ribbons can store energy and can be used to transmit the energy efficiently with high spatial resolution to the target location (e.g., the calcified valve, vessel, or tissue). A programmable high-density power supply from one or more wide-bandgap semiconductors (e.g., gallium nitride (GaN) semiconductors) can be used.

Embodiments of the subject invention provide at least the following three key innovations: 1) storing energy in soft nanocrystalline magnetic ribbons that need low ampere-turns or low power to achieve the required field; 2) transmitting this energy efficiently with high spatial resolution (i.e., a resolution of sub-millimeter (mm) in a region within a few mm (e.g., less than 10 mm) from the catheter) to the target location using the magnetic nanoribbon transcatheter technology; and 3) programmable high-density power supplies from wide-bandgap semiconductors (e.g., GaN semiconductors) to achieve the target dynamic field intensities and time-dependent field gradients at low power and small size (i.e., the magnetic fields can be generated with a power of 0.1 W-10 W with cables of thickness of 1 mm-5 mm to generate a target field over an airgap on the order of millimeters).

Other than heart valve replacement with a prosthetic valve for critical CAVD, there is no other means of treatment that is currently available. Therefore, the packaging of magnetic field therapy in the form of a transcatheter system, as in embodiments of the subject invention, to safely and effectively restore the native aortic valve function is a game-changer in the field of heart valve disease. In other words, diseased valves can be corrected to restore their function rather than being replaced with an artificial valve. While a mature technology, mechanical heart valves require life-long anti-coagulant therapy while bio-prosthetic valves from porcine and bovine sources have limited durability of 8-15 years. Therefore, restoration of function of a diseased native aortic human heart valve can facilitate a larger target of recipients (e.g., younger patients with CAVD) than prosthetic valves.

Embodiments of the subject invention address the clinical problem of acquired CAVD, which is a fairly common cardiovascular disorder, particularly among adults over the age of 65 years old. The build-up of calcific deposits on the aortic heart valve leads to its malfunction, and eventually to heart failure if left untreated. The only related art treatment modality currently available is artificial valve replacement, which has its own limitations such as clot formation, limited durability, and high cost of the procedure. However, if these calcified deposits are safely removed from the affected valve, it is possible that the valve function will be restored without the need for a valve replacement, with subsequent calcific build-up leading to a recurring valve malfunction only after several years.

Pulsed magnetic fields in nonmedical applications (e.g., in industrial pipes in buildings) can be used to destabilize calcium compounds leading to their removal and thereby restoring fluid transport in these systems. The data collected (see, e.g., Example 1) show that a pulsed magnetic field transcatheter system for aortic valve decalcification, according to embodiments of the subject invention, can be used to effectively treat critical CAVD, thereby restoring native aortic heart valve function and eliminating or inhibiting the need for artificial or prosthetic valve replacement.

An aim of embodiments of the subject invention is to optimize magnetic field treatment for de-calcification of valve tissue (e.g., human valve tissue such as engineered human valve tissues). An engineered model system of severely calcified engineered human valve extracellular matrix (ECM) was developed and can be used as a testbed to optimize the magnetic field therapy of embodiments of the subject invention. The initial results show the effect at about 60 minutes of treatment time. Because the frequencies are low (e.g., 1 Hertz (Hz)-1000 Hz), no major safety issues are anticipated for these field levels and treatment times. Valve function pre- and post-treatment can then be assessed hydrodynamically using a pulse duplicator system to quantify the valve's efficacy after treatment, via its effective orifice area (EOA), transvalvular pressure gradient, forward flow, and/or regurgitant (leakage) volume. In addition, histological characterization (e.g., Alizarin Red) can be conducted to directly evaluate the extent of calcified deposits that were removed following treatment. In addition, evidence of the intactness of the valve ECM and its phenotype post-treatment can be determined (e.g., via Movat's Pentachrome histology and CD31/α-SMA immunostaining, respectively).

An aim of embodiments of the subject invention is to provide a transcatheter magnetic field decalcification system with safe capture and removal of the valve calcified deposits. The magnetic field source can be miniaturized in the form of ribbons that can be encapsulated within a transcatheter system that can also include an inflatable balloon and/or filtration system to capture decalcified particles from the valve for safe and effective removal from the patient (see also FIG. 1).

In some embodiments, a magnetic field generator can be used to generate magnetic fields in the transcatheter valve decalcification system/method. The field generator can be integrated with a transcatheter to achieve the benefits discussed herein. The field generator can provide a magnetic field while the catheter is within the patient (e.g., at or near the target site having the calcification) and can cause the pulsed magnetic field ribbons to release their stored energy. The field generator can provide the magnetic field wirelessly (e.g., while being outside the patient while the catheter is disposed within a valve or other vessel or tissue of the patient).

The transitional term "comprising," "comprises," or "comprise" is inclusive or open-ended and does not exclude additional, unrecited elements or method steps. By contrast, the transitional phrase "consisting of" excludes any element, step, or ingredient not specified in the claim. The phrases "consisting" or "consists essentially of" indicate that the claim encompasses embodiments containing the specified materials or steps and those that do not materially affect the basic and novel characteristic(s) of the claim. Use of the term "comprising" contemplates other embodiments that "consist" or "consisting essentially of" the recited component(s).

When ranges are used herein, such as for dose ranges, combinations and subcombinations of ranges (e.g., subranges within the disclosed range), specific embodiments therein are intended to be explicitly included. When the term "about" is used herein, in conjunction with a numerical value, it is understood that the value can be in a range of 95% of the value to 105% of the value, i.e. the value can be +/−5% of the stated value. For example, "about 1 kg" means from 0.95 kg to 1.05 kg.

The methods and processes described herein can be embodied as code and/or data. The software code and data described herein can be stored on one or more machine-readable media (e.g., computer-readable media), which may include any device or medium that can store code and/or data for use by a computer system. When a computer system and/or processor reads and executes the code and/or data stored on a computer-readable medium, the computer system and/or processor performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that are capable of storing computer-readable information/data. Computer-readable media should not be construed or interpreted to include any propagating signals. A computer-readable medium of embodiments of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

A greater understanding of the embodiments of the subject invention and of their many advantages may be had from the following examples, given by way of illustration. The following examples are illustrative of some of the methods, applications, embodiments, and variants of the present invention. They are, of course, not to be considered as limiting the invention. Numerous changes and modifications can be made with respect to embodiments of the invention.

Example 1

Figure 2A:
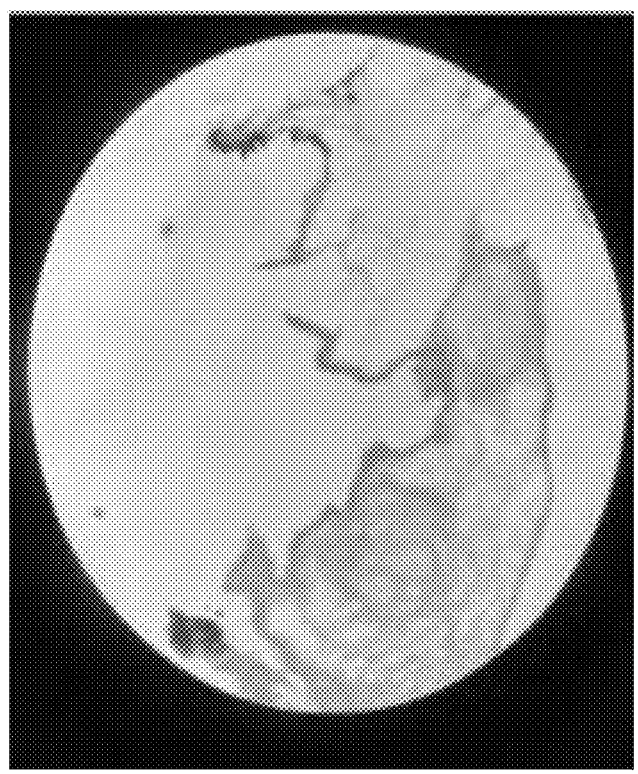
FIGS. 2(a) and 2(b) show views of porcine heart valve tissues that were cultured under calcification-inducing media.
Figure 2B:
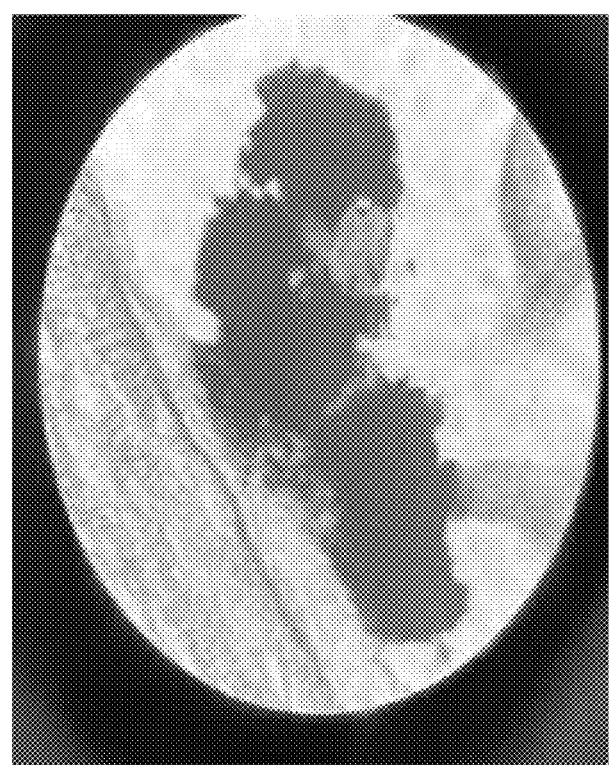

A pulsed magnetic field protocol was used on porcine heart valve tissues to demonstrate how systems and methods of embodiments of the subject invention can effectively remove calcified deposits from heart valve tissue. Two porcine heart valve tissues were first cultured under calcification-inducing media. One was left untreated, and the other was treated (after the culturing) with a pulsed magnetic field of 50 Gauss (frequency of 5 Hertz (Hz) and potential of 5 Volts (V)) and 300 Gauss (1 Hz, 22 V) for 30 minutes each. After the treatment (for the sample that was treated), both samples (treated and untreated) were simultaneously processed histologically using Alizarin red staining. FIGS. 2(a) and 2(b) show the resulting untreated and treated tissues, respectively, with red stains indicating regions of high calcification. It can be seen that the treated tissue (FIG. 2(b)) had almost no calcification remaining after the pulsed magnetic field protocol while the untreated tissue had a large amount of calcification.

Example 2

Human Valve Interstitial Cells (HVICs), which are commercially available (Lonza, Inc, Walkersville, MD), will be seeded onto 3-dimensional tubular valve bioscaffolds (porcine small intestinal submucosa (PSIS); Cormatrix, Roswell, GA). After 8 days of tissue culture, the constructs will be exposed to a pro-calcific media for a period of 7 days to induce severe levels (>70% of the surface area) of calcified deposits onto the engineered valve tissues. The calcification media includes Dulbecco's Modified Eagle Medium (DMEM), $CaCl_2$, $NaH_2PO_4$, and inorganic pyrophosphatase. The severe calcification of the engineered valve tissue constructs will be confirmed via Alizarin red histology. The engineered tissue valves with severe levels of calcified deposits will then be hydrodynamically tested in a pulse duplicator system (Vivitro Labs, Victoria, BC), with the valves mounted in the aortic position. A prosthetic valve will be placed in the mitral position. Specific hydrodynamic metrics to be measured under systemic circulation flow conditions will include: i) the valve effective orifice area (EOA); ii) the percentage of forward flow; iii) the leakage or regurgitation fraction; and iv) the transvalvular pressure gradient.

Figure 3:
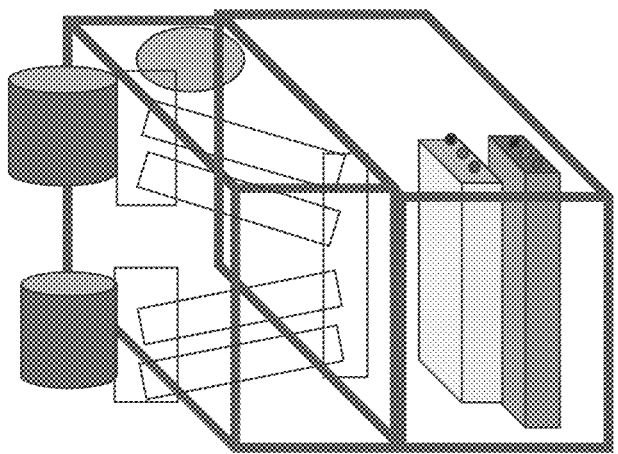
FIG. 3 shows an image of a magnetic field therapy accelerator that can be used with embodiments of the subject invention. In the text description next to the image, A stands from Amperes, cm stands for centimeters, T/second stands for Tesla per second, and C/° C. stands for degrees Celsius. The values given in the text description are for exemplary purposes only and should not be construed as limiting.

A magnetic field generator can be used to achieve the decalcification, and fabrication of customized magnetic field generators can be considered. Prior work at Florida International University (FIU) focused on an external magnetic field therapy accelerator (FTA). The FTA is shown in FIG. 3. An in-house magnetic field therapy system was built that can produce 500-1000 Gauss and switching frequency of 10-100 Hz, resulting in magnetic field gradients that approach 1 Tesla per second (T/second). The resulting FTA (FIG. 3) includes two electromagnets that face each other. The gap between them can be adjusted using a signalized crank below the electromagnets. This feature allows the user to change the area to fit the needs of the treatment. A field programmable gate array (FPGA) driver can be used in the system in order to control two insulated-gate bipolar transistors (IGBT) that power each electromagnet. By synchronizing the two outputs in the driver and including the second IGBT to switch on/off the second electromagnet with high and low signals of identical shape and frequency, a larger variation of the magnetic field can be created, leading to better therapeutic effects in the tissue. The electronic control and the power supply can be securely tightened at the bottom of the device to allow for visual inspection and ventilation. A set of retractable wheels can also be included to facilitate the transportation of the FTA. The main limitation in achieving higher fields was the coil heating at higher currents, which required convectional cooling with a fan. The current provided to the electromagnets was limited to 5.58 Amperes (A). This limitation was imposed to maintain the electromagnet temperature below 43° C. without the need for a cooling system. However, when the two electromagnets are working for an extensive period, and the gap between them is considerably small, the temperature at the surface can increase up to 50° C. This temperature increment can be dissipated by placing the equipment in a ventilated room at all times. With the chosen current value, each electromagnet can generate up to 0.3 Tesla (T) in the core. This system was used in the initial decalcification results reported in Example 1, in which the fields were limited to 300 Gauss so that the temperature increments were minimal and did not affect the sample.

The FTA will be extended to an integrated field generator in a magnetic transcatheter system. The field generator can be integrated with a transcatheter to achieve the benefits discussed herein.

Magnetic flux generators will be integrated with high permeability nanomagnetic layers (perceived as magnetic field amplifiers) to amplify the generated magnetic field to over 0.5 T using low currents to achieve a wider field tunability range by programming the current generator. The reluctance in the magnetic loop is reduced to lower the power requirements. Because reluctance is proportional to the length of the core ($l_c$) and inversely related to the low cross-sectional area ($A_c$) of the transcatheter, high permeability ribbons or composites are needed to enhance the flux. The magnetic field generators will be improved with nanoscale magnetocrystalline soft cores that act as flux transmitters and concentrators. Controlled pulsed magnetic fields will be generated from small currents applied to the coils in the transcatheter. The high permeability (~60,000) of these films will aid in generating strong fields with minimal N×I (number of turns x current). The metallic nanoribbons can be designed to accommodate the transcatheter geometries. The nanoribbon core transcatheter can be modeled in COMSOLTM and ANSYS-Maxwell to identify the optimal currents in each coil and to obtain the designed field gradients. The role of shape anisotropy, joule heating, and material magnetic flux density-magnetic field strength product (BH) to achieve the required field at the target distance will be determined. With customized coil designs and nanocrystalline integration, the required local magnetic fields can be generated with smaller coil currents (about 0.25 A) and lower total coil resistances (less than 0.1 Ohm). Compact low-power programmable three-dimensional (3D) magnetic field generators can thus be fabricated with high field strength and gradients in deep tissues.

After magnetic field therapy optimization, the valves will be re-tested hydrodynamically to assess if there is any improvement in function. Subsequently, histological analysis will be performed to identify the level of calcified deposits reduced as well as the maintenance of the engineered valve tissues ECM composition in comparison to engineered valve tissues without exposure to pro-calcifying media.

Example 3

Given the unacceptable risk of stroke after transcatheter aortic valve replacement (TAVR), several efforts are clinically underway to combine TAVR deployment with a secondary device classified as a cerebral embolic protection system (CEPS) (see, e.g., Schmidt et al., Debris Heterogeneity Across Different Valve Types Captured by a Cerebral Protection System During Transcatheter Aortic Valve Replacement, JACC Cardiovasc Intery 11(13), 1262-1273, 2018; which is hereby incorporated by reference herein in its entirety). A CEPS includes filters that trap calcified particles (greater than 1 millimeter (mm) in diameter or greatest width) that are unintentionally released in key arteries (e.g., carotid artery) from the native, diseased valve during TAVR deployment. The system can remove calcified particles that are wished to be intentionally removed from the native valve via, e.g., one or more filters present in the catheter and/or one or more balloons present in the catheter. A transcatheter valve decalcification system of an embodiment of the subject invention can be assessed in vivo.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein are incorporated by reference in their entirety, including all figures and tables, to the extent they are not inconsistent with the explicit teachings of this specification.

What is claimed is:

1. A method for decalcifying a valve, a blood vessel, or a cardiac tissue of a mammalian patient, the method comprising:
    inserting a catheter into an internal structure of the patient, the internal structure having calcium compounds therein, and the catheter comprising a lumen, a wall, at least one inflatable balloon disposed within the lumen of the catheter, a plurality of pulsed magnetic field ribbons encapsulated within the wall of the catheter, and at least one filter disposed within the lumen of the catheter substantially orthogonal to blood flow within the internal structure of the patient and configured to entrap de-calcified particles spatially;
    providing a magnetic field to the plurality of pulsed magnetic field ribbons in a manner that the plurality of pulsed magnetic field ribbons release stored energy, transmit the stored energy with spatial resolution less than 10 mm from the catheter to a target location within the internal structure, and destabilize the calcium compounds into forming the de-calcified particles;
    entrapping at least a portion of the de-calcified particles with the at least one filter;
    inflating the at least one inflatable balloon to collect the entrapped de-calcified particles; and
    removing the catheter from the internal structure of the patient,
    the pulsed magnetic field ribbons being soft nanocrystalline magnetic ribbons configured to generate a magnetic field of 0.5 Tesla (T) to 2 T,
    the magnetic field being provided by a magnetic field generator,
    the method further comprising providing power to the magnetic field generator with a programmable high-density power supply in operable communication with the magnetic field generator, and
    the programmable high-density power supply comprising a wide-bandgap semiconductor.

2. The method according to claim 1, the pulsed magnetic field ribbons being configured to generate the magnetic field of 1.5 T to 2 T.

3. The method according to claim 1, the magnetic field generator providing the magnetic field to the plurality of pulsed magnetic field ribbons while the catheter is inserted into the internal structure of the patient.

4. The method according to claim 3, the magnetic field generator wirelessly providing the magnetic field to the plurality of pulsed magnetic field ribbons while the catheter is inserted into the internal structure of the patient.

5. The method according to claim 1, the wide-bandgap semiconductor being a wide-bandgap gallium nitride (GaN) semiconductor.

6. The method according to claim 5, the pulsed magnetic field ribbons being configured to generate the magnetic field of 0.5 T to 2 T with input currents of 0.1 Amperes (A) to 1 A and amp-turns of 0.1 to 1 supplied by the programmable high-density power supply.

7. The method according to claim 5, the pulsed magnetic field ribbons being configured to generate the magnetic field of 0.5 T to 2 T with input currents of 200 Ampere/meter, amp-turns of 0.1 to 1 and power of 0.1 Watt (W) to 10 W supplied by the programmable high-density power supply.

8. The method according to claim 5, the pulsed magnetic field ribbons being configured to generate the magnetic field of 1.5 T to 2 T with input currents of 0.1 Amperes (A) to 1 A and amp-turns of 0.1 to 1 supplied by the programmable high-density power supply.

9. The method according to claim 5, the pulsed magnetic field ribbons being configured to generate the magnetic field of 1.5 T to 2 T with input currents of 200 Ampere/meter, amp-turns of 0.1 to 1 and power of 0.1 Watt (W) to 10 W supplied by the programmable high-density power supply.

10. The method according to claim 1, the pulsed magnetic field ribbons being configured to generate the magnetic field of 0.5 T to 2 T with input currents of 0.1 Amperes (A) to 1 A and amp-turns of 0.1 to 1 supplied by the programmable high-density power supply.

11. The method according to claim 1, the pulsed magnetic field ribbons being configured to generate the magnetic field of 0.5 T to 2 T with input currents of 200 Ampere/meter, amp-turns of 0.1 to 1 and power of 0.1 Watt (W) to 10 W supplied by the programmable high-density power supply.

12. The method according to claim 1, the pulsed magnetic field ribbons being configured to generate the magnetic field of 1.5 T to 2 T with input currents of 0.1 Amperes (A) to 1 A and amp-turns of 0.1 to 1 supplied by the programmable high-density power supply.

13. The method according to claim 1, the pulsed magnetic field ribbons being configured to generate the magnetic field of 1.5 T to 2 T with input currents of 200 Ampere/meter, amp-turns of 0.1 to 1 and power of 0.1 Watt (W) to 10 W supplied by the programmable high-density power supply.

14. The method according to claim 1, the pulsed magnetic field ribbons having a pulsating frequency in a range of from 1 Hertz (Hz) to 1000 Hz.

15. A method for decalcifying a valve, a blood vessel, or a cardiac tissue of a mammalian patient, the method comprising:
    inserting a catheter into an internal structure of the patient, the internal structure having calcium compounds therein, and the catheter comprising a lumen, a wall, at least one inflatable balloon disposed within the lumen of the catheter, a plurality of pulsed magnetic field ribbons encapsulated within the wall of the catheter, and at least one filter disposed within the lumen of the catheter substantially orthogonal to blood flow within the internal structure of the patient and configured to entrap de-calcified particles spatially;

providing a magnetic field to the plurality of pulsed magnetic field ribbons in a manner that the plurality of pulsed magnetic field ribbons release stored energy, transmit the stored energy with spatial resolution less than 10 mm from the catheter to a target location within the internal structure, and destabilize the calcium compounds into forming the de-calcified particles;

entrapping at least a portion of the de-calcified particles with the at least one filter;

inflating the at least one inflatable balloon to collect the entrapped de-calcified particles; and removing the catheter from the internal structure of the patient, the magnetic field being provided by a magnetic field generator, the magnetic field generator wirelessly providing the magnetic field to the plurality of pulsed magnetic field ribbons while the catheter is inserted into the internal structure of the patient, the method further comprising providing power to the magnetic field generator with a programmable high-density power supply in operable communication with the magnetic field generator, the programmable high-density power supply comprising a gallium nitride (GaN) wide-bandgap semiconductor, and the pulsed magnetic field ribbons being soft nanocrystalline magnetic ribbons configured to generate a magnetic field of 0.5 Tesla (T) to 2 T with input currents of 0.1 Amperes (A) to 1 A and amp-turns of 0.1 to 1 supplied by the programmable high-density power supply.

16. The method according to claim 15, the pulsed magnetic field ribbons being configured to generate the magnetic field of 1.5 T to 2 T.

17. The method according to claim 15, the pulsed magnetic field ribbons having a pulsating frequency in a range of from 1 Hertz (Hz) to 1000 Hz.

* * * * *